United States Patent [19]

Hall et al.

[11] Patent Number: 4,496,355
[45] Date of Patent: Jan. 29, 1985

[54] EXTERNAL FEMALE URINARY APPLIANCE

[75] Inventors: Kenneth F. Hall, Arvada, Colo.; William H. Beecher, Elmhurst, Ill.

[73] Assignee: Illinois Tool Works Inc., Chicago, Ill.

[21] Appl. No.: 442,068

[22] Filed: Nov. 16, 1982

[51] Int. Cl.³ .......................... A61M 1/00; A61F 5/44
[52] U.S. Cl. .................................... 604/327; 4/144.3; 604/329
[58] Field of Search ................ 128/760; 604/327–331, 604/353, 338, 343, 347; 4/144.1–144.3

[56] References Cited

U.S. PATENT DOCUMENTS

| 3,520,305 | 7/1970 | Davis | 604/349 |
| 3,995,329 | 12/1976 | Williams | 604/329 |
| 4,198,979 | 4/1980 | Cooney et al. | 604/331 |

FOREIGN PATENT DOCUMENTS

| 0018749 | 11/1980 | European Pat. Off. | 604/347 |
| 996370 | 6/1965 | United Kingdom | 4/144.3 |
| 2070936 | 9/1981 | United Kingdom | 604/329 |

Primary Examiner—C. Fred Rosenbaum
Assistant Examiner—J. L. Kruter
Attorney, Agent, or Firm—David I. Roche; J. R. Halvorsen; T. W. Buckman

[57] ABSTRACT

A one-piece external female urine collection device is disclosed. The device is adapted to be positioned within the labia folds of the user, and to be in contact with the vestibular tissue around the meatus defining the urethral opening. The device includes a generally ovoid and cup-shaped member, and has a generally centrally disposed bore opening so that urine can flow through the member and the device. The upper periphery of the member has a generally convexly curved exterior surface and a substantially continuously curved ridge extending upwardly therefrom defining upper portions of a cavity within the member. The upper periphery and the ridge define a generally adjacent pair of sealing surfaces. The inner surface is generally disposed farther upwardly relative to the outer. The adjacent surfaces permit the device to sealingly and continuously make contact with the female by engaging with the labia folds and the above-mentioned vestibular tissue. The device includes a drainage channel which is integral with a backside of the member and which communicates with the bore opening. The device further includes means for preventing the drainage channel from kinking.

12 Claims, 11 Drawing Figures

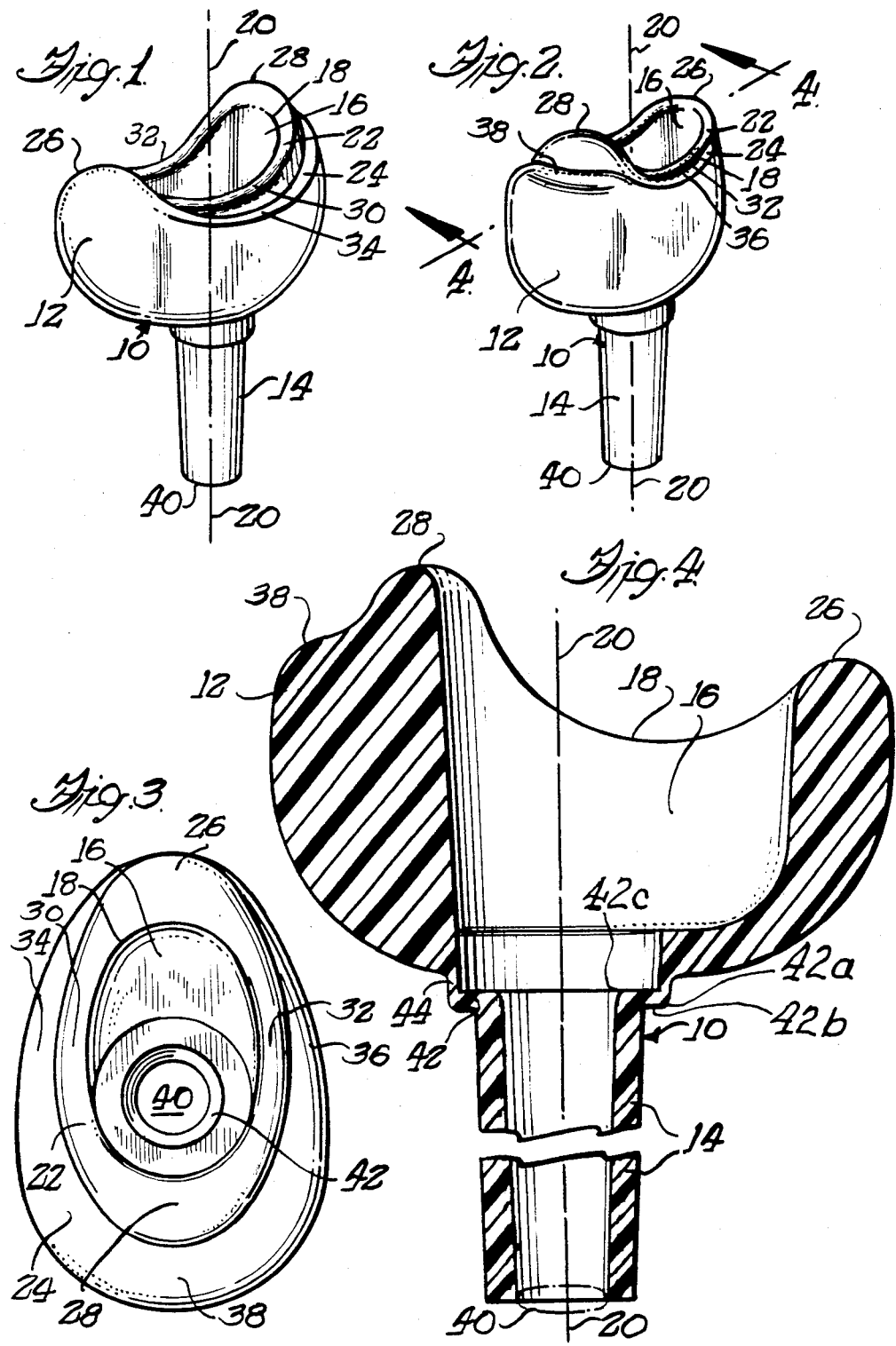

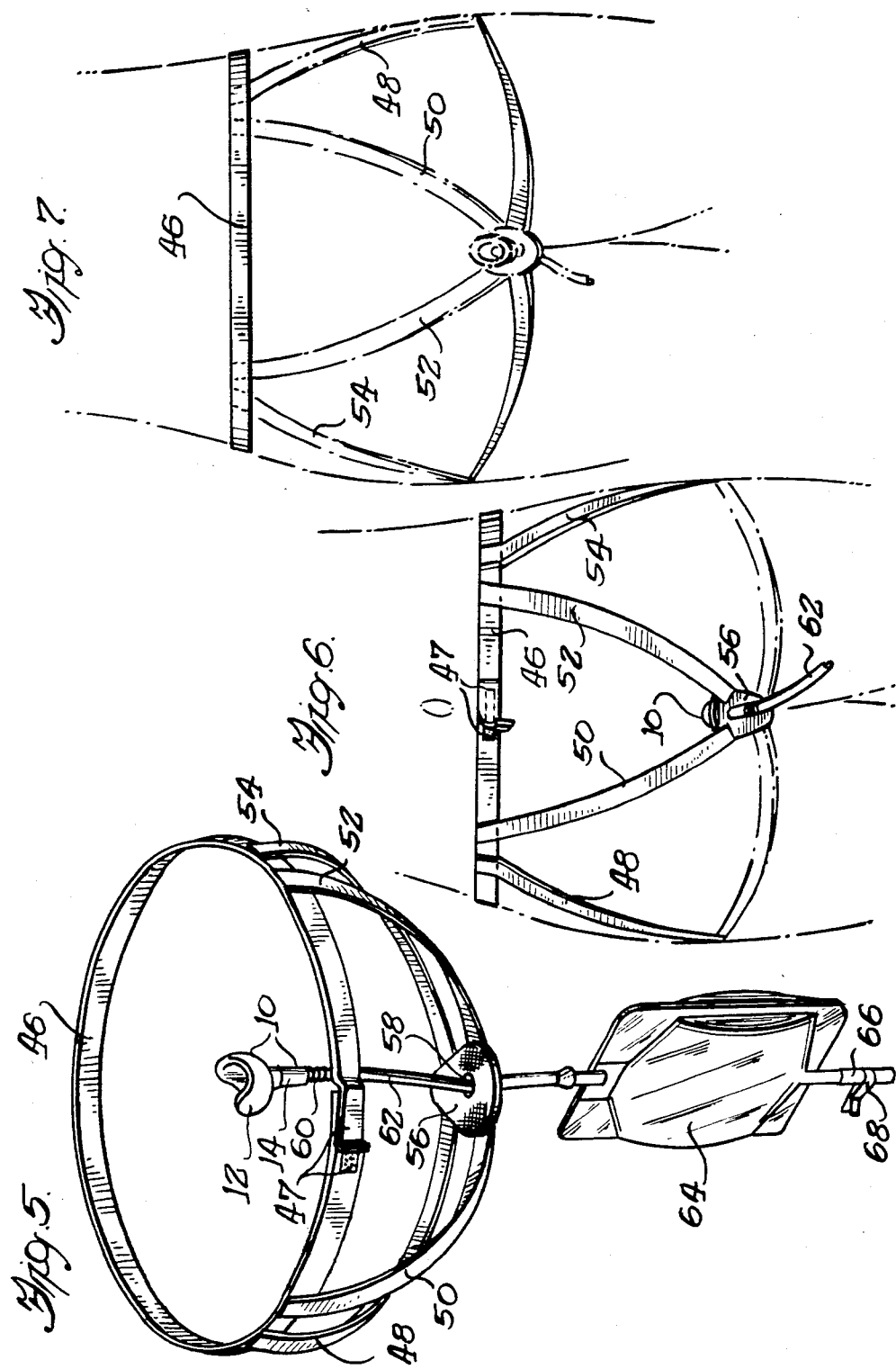

EXTERNAL FEMALE URINARY APPLIANCE

BACKGROUND OF THE INVENTION

This invention relates to a field of human urinary appliance or devices which have been adapted to be held in place exterior to the human form; and more particularly, this invention relates to a field of urinary appliances which have been specifically adapted to be gently held in place essentially exterior to the female human form. The appliance has been found effective when used by a subject who is in an upright, sitting, or generally supine position.

Certain paraplegic, quadriplegic, incontinent, and other female human subjects often require assistance when relieving the urinary bladder of urine. The female urinary appliance industry manufactures a variety of devices adapted to provide different degrees of assistance to such subjects. One problem the female urinary appliance industry faces is manufacture of an appliance which is easily worn and which does not leak when in use. This essentially means that the appliance must not only be capable of being secured to the female human form by commercially available securement means and of being held snugly in place by such securement means, but it also means that the appliance must provide an effective and otherwise non-leaking seal when applied to the female human form (or outer surface of the body). In addition, these appliances must be non-binding, non-pinching, non-irritating, resilient, elastic, sterile, aseptic and generally somewhat smooth and soft to the touch.

Much of the prior art has not addressed the leakage problem associated with bodily engagement of a particular urinary appliance upon the female human form; and therefore, much of the female urinary appliance prior art has avoided claiming a leak-free urinary appliance. The key to the leak-free feature of any female urinary appliance is the way in which such appliance engages the female human form.

Many of the difficulties associated with a female urinary appliance making a sealing engagement with the female human form naturally grow out of the unique nature of the external female organs of generation which, of course, surround the orifice of the urethra. Reference to FIG. 8 is herein made to illustrate engagement of the appliance with generally recognized female bodily surfaces.

Medical authority teaches us that the external organs of generation in the human female are the mons Veneris, the labia majora and minora, the clitoris, the meatus urinarius, and the orifice of the vagina; and further defines the term "vulva" or "pudendum" to include all these parts. In addition, the "vestibule", as used in connection with the female human form, is medically defined to be located in a triangularly shaped, smooth region between the clitoris and the entrance of the vagina, and bounded on each side by the labia minora. Lastly, medical authority teaches us that the meatus urinarius (also referred to as the orifice of the urethra) is situated at a back (or lower) part of the vestibule, about an inch below the clitoris, near the margin of the vagina, and that the meatus urinarius is surrounded by a prominent elevation of a mucous membrane (also referred to as the mucosa).

It is an object of the present invention to provide a female urinary appliance which can make a leak-free sealing engagement with the female human form, while the subject is in a standing, sitting, or generally supine position.

It is also an object of the present invention to provide a leakfree female urinary appliance which provides the subject with only a relatively minor degree of discomfort when worn.

These and other objects of the present invention will become clear upon reading the detailed description and upon making reference to the drawings contained herein.

SUMMARY OF THE PRESENT INVENTION

In accordance with the objects of the present invention, there is herein disclosed a female urinary appliance adapted to sealingly externally engage the female human form. The female urinary appliance of the present invention can be used to collect urine from a subject in a semi-continuous or even a continuous manner. Furthermore, the present invention can be used by the female human subject to collect urine while the subject is in an upright or standing position, a generally supine position or a sitting position.

The appliance seals when gently held in place. The appliance firstly makes a sealing engagement against the mucous membrane surrounding the meatus urinarius and secondly makes a sealing engagement against the vestibule. To make such a dual-natured sealing engagement, the appliance has been provided with a pair of raised sealing surfaces. Gentle pressure applied to a backside or underside of the appliance located opposite a urine-receiving cavity causes one of the two raised sealing surfaces and a raised portion of the appliance to co-operate to force tissue surrounding the meatus urinarius to protrude markedly into the urine-receiving cavity of the appliance, thereupon directing a stream of urine exiting the urethral orifice into such cavity. The sealing engagement of the appliance is additionally enhanced by nature of the general frontal shape and surface geometry of the sealing surfaces, which have been adapted to essentially match the angle and body surfaces of the vestibule of the female human form.

More particularly, the appliance sealingly engages the vestibule and isolates the orifice of the urethra from the orifice of the vagina. Bodily engagement with the vestibule comprises a series of sealing engagements between the labia minora, the meatal prominence between the orifice of the vagina and the orifice of the urethra, and certain other tissue located proximate to the clitoris but disposed slightly away from the clitoris in the direction of the orifice of the urethra.

BRIEF DESCRIPTION OF THE DRAWINGS

FIG. 1 is a perspective view looking down upon a portion of a pair of sealing surfaces located around the cavity at the urine receiving end of the appliance;

FIG. 2 is a second perspective view of the appliance, again looking down upon the sealing surfaces as in FIG. 1, but with the appliance rotated approximately 180 degrees about a central axis;

FIG. 3 is a top view looking down upon the urine-receiving cavity of the appliance, illustrating the essentially egg-shaped nature of the sealing surfaces;

FIG. 4 is a sectional side view of the female appliance, taken along line 4—4 of FIG. 2, illustrating an anti-kinking feature of a drainage channel which is adapted to permit urine to flow freely out of the cavity, even after the drainage channel is disposed away from the central axis by as much as 90 degrees;

FIG. 5 is a perspective illustration of the appliance functionally connected to a fluid reservoir and used in connection with a preferred form of a commercially available bodily securement and collection device;

FIG. 6 is a perspective illustration of a frontal view of the preferred form of the bodily securing device;

FIG. 7 is a perspective illustration of a rear view of the preferred form of the bodily securing device, as the securing device engages the female human form;

Throughout the drawings, like reference numerals refer to like parts.

DETAILED DESCRIPTION OF THE PREFERRED EMBODIMENT

Figure 4A:
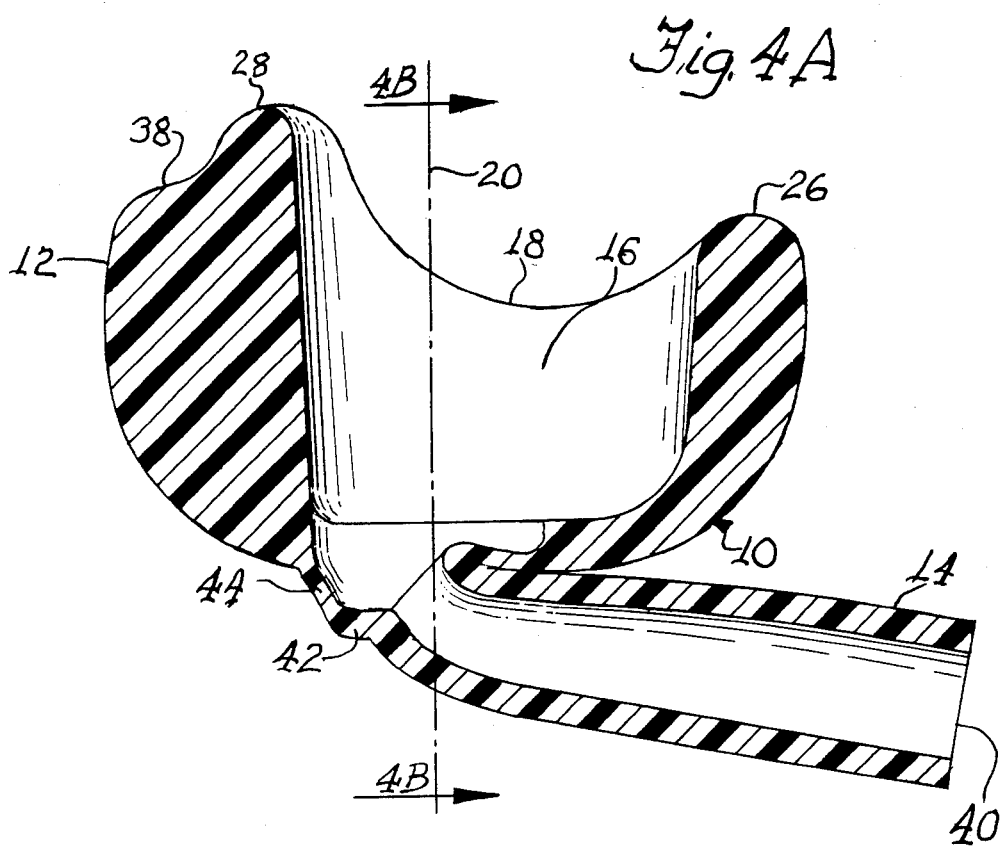
FIG. 4A is a sectional side view of the female appliance similar to FIG. 4 except that the drainage channel is bent and disposed in a position substantially 90 degrees from that shown in FIG. 4 to more clearly illustrate the efficacy of the anti-kinking feature.

Turning now to FIG. 1, the appliance 10 is shown in perspective and comprises a receptacle 12 and a hollow stem 14. The receptacle 12 contains a cavity 16. The cavity 16 has an entrance opening 18 which is essentially a vertical extension of the cavity 16.

The cavity 16 is essentially radially oriented about a central axis 20; and the receptacle 12 has a generally ovoid or egg-shaped external perimeter and a generally elliptical or oval-like inner cross section both of which are oriented perpendicularly to the central axis 20.

The opening 18 is provided with two generally elliptical sealing surfaces 22, 24 generally convex in section. Each sealing surface protrudes from the receptacle 12 in a saddle-like fashion along the direction of the central axis 20. Each sealing surface, in side view, is provided with two ridges interposed between two peaks (or summits), and each peak is positioned proximate to a respective end of the major axis of the receptacle 12.

The first (or inner) substantially continuous sealing surface 22 is provided with a first or front peak 26 which is adapted to sealingly engage with the female human form at a first point just below the clitoris. Such first point is generally located between the clitoris and the orifice of the urethra, and is usually located proximate to the clitoris, but slightly displaced from the clitoris in the direction of the orifice of the urethra. The inner sealing surface 22 is also provided with a second or rear peak (or "hump") 28 which is adapted to sealingly engage with the female human form at a second point located between the orifice of the urethra and the orifice of the vagina. The inner sealing surface 22 is provided with a first pair of spaced oppositely disposed side or connecting ridges 30, 32 which are adapted to sealingly engage with the underside or inner surfaces of the two labia minora along an opposed pair of first elliptical regions.

The second (or outer) sealing surface 24 is positioned essentially along the outer periphery of the first sealing surface 22. The surface contours of the outer sealing surface 24 are blended into the first sealing surface 22 at the first peak 26. The second sealing surface 24 is also provided with a second pair of ridges 34, 36 which similarly are adapted to sealingly engage with the two labia minora along an opposed pair of second elliptical or oval regions. Except for the blend of surface 24 with peak 26, each respective second elliptical or oval region is displaced slightly away, both radially and axially, from its adjacent first elliptical region, as illustrated in FIGS. 1 and 2.

The outer sealing surface 24 is provided with another peak 38 which is adapted to sealingly engage with the female human form at a third point located between the second point and the orifice of the vagina.

The surface geometry of the receptacle 12 is such that the inner sealing surface 22 generally protrudes out and farther away from the main portion of the receptacle 12 than does the outer sealing surface 24. Such protrusion is in a saddle-like fashion and is along the direction of the central axis 20.

The surface contours of the inner sealing surface 22 and the outer sealing surface 24 are convexly curved in an outward direction, the curvature being positively directed away from the cavity 16. In addition, the inner sealing surface 22 smoothly blends into the cavity 16, thereby providing the opening 18.

The inner sealing surface 22 and the outer sealing surface 24 each has a wall sufficiently thick that the inner sealing surface 22 and the outer sealing surface 24 each maintains its shape and does not deform when the urinary appliance 10 is held in place against the female human form by gentle pressure generally applied along a backside or underside of the receptacle 12 opposite the cavity 16. The inner and the outer sealing surfaces 22, 24 of the appliance 10 each permit the appliance 10 to make a sealing engagement with the tissue surrounding the meatus urinarius. The surface curvature, saddle-like contours and elliptical cross section of the two sealing surfaces of the appliance 22, 24, and more particularly, the raised "hump" or peak 28 of the inner sealing surface 22, cooperate with the outer sealing surface 24 to produce a gentle bulging of meatal (meatus urinarial) prominence into the cavity 16 of the appliance 10, thereby causing the stream of urine to be directed into the receptacle cavity 16.

The dual sealing surfaces serve two purposes. First, if a sample of urine is to be used for analysis, it will not be contaminated by vaginal discharge; and second, the normal menstrual cycle can be separately attended to through the ordinary use of commercially available catamenial devices without interfering with waste fluid handling.

Figure 8:
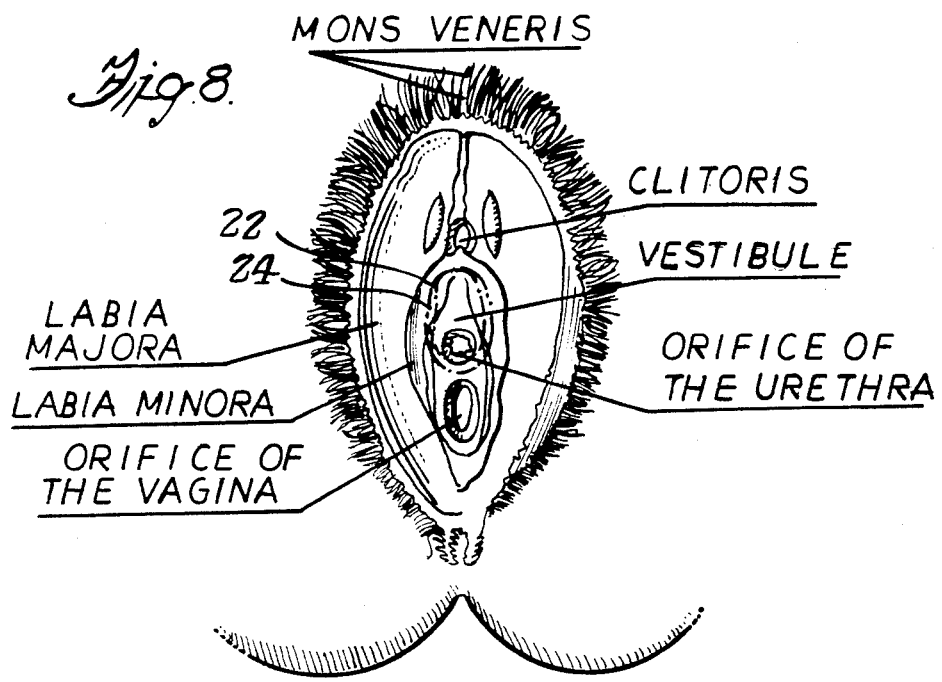
FIG. 8 is an illustration of the external female organs of generation showing regions of frontal engagement of the sealing surfaces of the appliance with the female human form.
Figure 9:
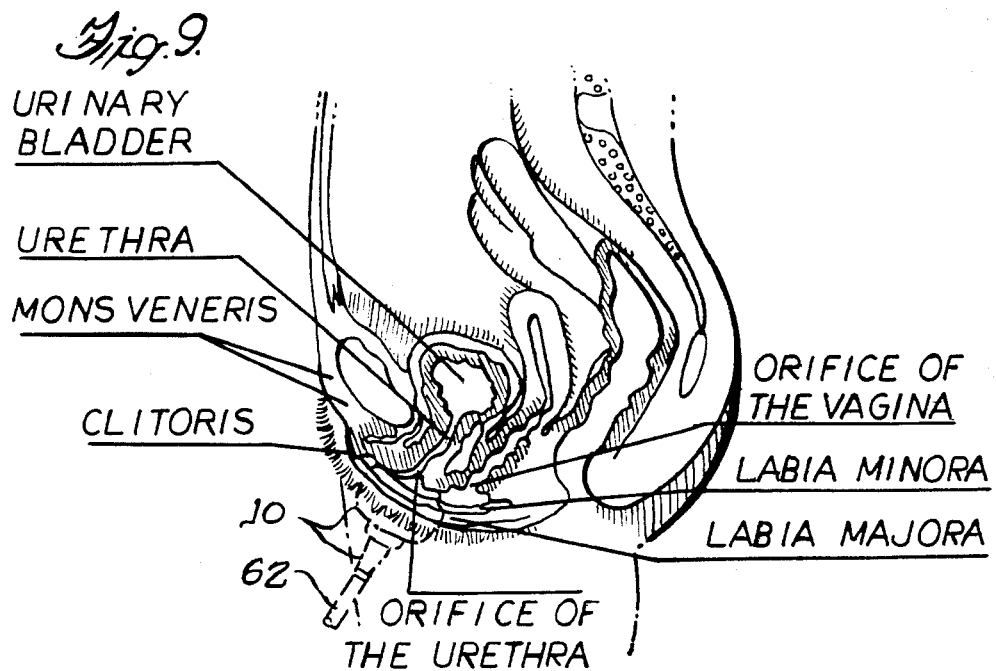
FIG. 9 is a vertical median section of the female pelvic region illustrating approximate orientation and bodily engagement of the appliance while the subject is either in an upright, a generally supine, or a sitting position.

FIGS. 1, 2 and 3 illustrate the surface geometry of the inner and the outer sealing surfaces 22, 24 of the appliance 10; and FIGS. 8 and 9 illustrate how the appliance 10 makes a sealing engagement with the female human form.

The hollow stem 14, shown in FIGS. 1, 2 and 4, is radially oriented about the central axis 20 and is integral with a portion of the backside or underside of the receptacle 12 opposite the cavity 16. The hollow stem 14 communicates with the cavity 16 and provides the cavity 16 with an outlet 40. Looking essentially down the central axis 20 and into the cavity 16, the inner diameter of the hollow stem 14 is essentially circular. The hollow stem 14 has a somewhat constant wall thickness, and has an outer diameter which progressively decreases, to a slight degree, moving outwardly from the receptacle 12.

The hollow stem 14 has a sufficient wall thickness and is made of a sufficiently resilient substance that "kinking", which normally would interfere with flow of urine out of the cavity 16, does not occur since the hollow stem 14 is provided with an "anti-kinking" feature including a hollow transitional portion 42 (which includes outside corner 42a horizonal flange 42b and inside corner 42c) and a hollow collar 44, to reduce the likelihood of kinking.

A drainage channel (for the cavity 16) is integral with the backside or underside of the receptacle 12 opposite the cavity 16 and includes the hollow stem 14, the hollow transitional portion 42, and the hollow collar 44. As illustrated in FIG. 4, the hollow stem 14 is integral with the hollow transitional portions 42a, b, and c; and the hollow transitional portions 42 are integral with the hollow collar 44 which is also integral with the backside or underside of the receptacle 12 opposite the cavity 16.

For the purposes of describing the drainage channel, the inner diameter of the hollow stem 14 progressively slightly decreases, moving outwardly and away from the main portion of the receptacle 12, while the hollow stem 14 wall thickness remains substantially constant. As a part of the anti-kinking feature of the drainage channel, the hollow stem 14 has a greater wall thickness than the hollow transitional portions 42a, 42b, and 42c which themselves have a greater wall thickness than the hollow collar 44.

Figure 4B:
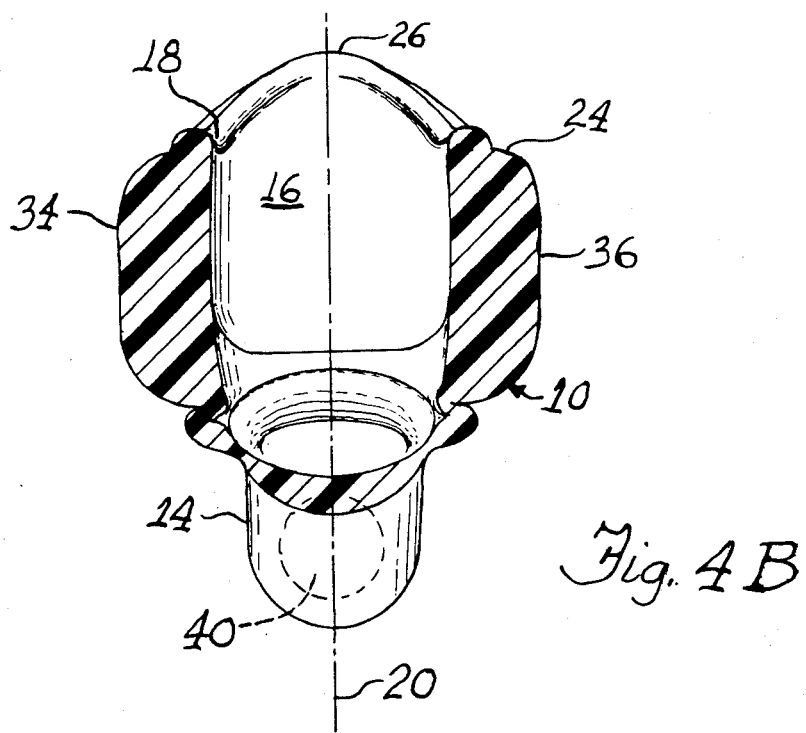
FIG. 4B is a sectional end view of the appliance shown in FIG. 4A when rotated 90 degrees along its drainage channel axis to illustrate the opening available through the anti-kinking feature.

The hollow nature of the stem 14, the transitional portion 42 and the collar 44 permit communication between the cavity 16 and the outlet 40. The relatively thin-walled hollow collar essentially eliminates the detrimental effects caused by kinking when the drainage channel becomes bent during use. As can be seen in FIGS. 4a and 4b, the drainage channel can be bent up to 90 degrees away from the central axis 20 and substantially full flow from the outlet 40 is maintained.

The progressively reduced thickness of the various elements moving axially upwardly from stem 14 through transition portion 42 into the hollow collar 44 permits the inward collapse of collar 44 on one side thereof to form at least an elliptical shaped opening, i.e. a somewhat flattened end to stem 14 where it is attacked to transition portions 42, that opens into the remaining interior of collar 44. This can be best seen in FIGS. 4A and 4B and insures an open drainage channel even when the stem 14 is moved substantially 90 degrees from its normal position when the patient moves from a standing or supine position to a sitting position.

Like the hollow stem 14, the hollow transitional portion 42 and the hollow collar 44 each has an essentially circular cross section. The outer diameter of the hollow collar 44 is significantly greater than the outer diameter of the hollow transitional portion 42, which itself is slightly greater than the outer diameter of the hollow stem 14.

When gentle pressure is applied in a direction generally parallel to the central axis 20 along the backside or underside of the receptacle 12, the inner and the outer sealing surfaces 22 and 24, and more particularly, the hump 28 co-operate to cause the inner and the outer sealing surfaces 22, 24 to effectively isolate, separately seal off, and provide the cavity 16 of the receptacle 12 with a pair of sealing engagements with the female human form. One sealing engagement is generally made around the orifice of the urethra. These dual sealing surfaces 22, 24 not only ensure a tight seal with minimum pressure, but also stabilize the appliance 10 against up and down or sideways movement.

The appliance 10 is manufactured from a suitable soft rubber, rubber-like or plastic substance.

The appliance 10 can be held in place against the female human form by any one of a variety of commercially available devices designed to bring the appliance into a sealing bodily engagement. For example, the appliance 10 can be held in place with a strap or belt arrangement. The described embodiment, illustrated in FIG. 5, shows just such an arrangement comprising a belt 46, four straps 48, 50, 52 and 54, and a pad 56.

The belt 46 is adapted to fit circumferentially around the waist of the subject and is manufactured from a suitably elastic material so that it will remain substantially in place when drawn downwardly by the action of the straps. The preferred belt is a commercially available variety made from a combination of cloth and elastic. The preferred belt has been provided with a commercially available closure device 47 ("VELCRO") to fit multiple waist sizes.

The four straps 48, 50, 52 and 54 also are made of a suitable elastic material so that the pad 56 is caused to apply gentle pressure to the backside or underside of the receptacle 12 opposite the cavity 16 when the belt-and-strap arrangement is worn by a subject who is in a standing, sitting or otherwise generally supine position. In the preferred embodiment, each strap comprises a cloth portion and an elastic portion. Each cloth portion is attached to the belt 46 and each elastic portion to the pad 56, as illustrated in FIGS. 5, 6 and 7. This manner of attachment causes the pad 56 to conform to the backside or underside of the receptacle 12 opposite the cavity 16, thereby effecting the above described sealing engagements. In the preferred embodiment the two lower (or outer) straps 48, 54, are illustrated in FIGS. 6 and 7, as passing on either side of the rectum, following the gluteal fold and thereafter being attached to the belt 46. In this embodiment, these lower straps 48, 54 are attached to the belt 46 either at the hipbone or at the anterior superior iliac spine of the pelvis. Also illustrated in FIGS. 6 and 7, are top (or inner) straps 50, 52 which have been adjacently attached to the belt 46 at positions proximate to the respective lower straps 48, 54. In the preferred embodiment, in addition to being elastic and therefore stretchable, these inner and outer straps are adjustable in length, as well.

The pad 56 is made of a suitable soft and pliable material. In the preferred embodiment, the side of the pad which is directed toward the female human form is made of a soft, felt-like material; while the backside of the pad, which is directed away from the female form, is fiber re-inforced. The preferred pad is somewhat disc-like in shape and somewhat larger in cross section than the cross section of the backside or underside of the receptacle 12 opposite the cavity 16, so that gentle pressure can be applied generally over the entire backside or underside of the receptacle 12 opposite the cavity 16. The straps 48, 50, 52 and 54 are usually attached to the outer periphery of the pad 56 in a fashion which permits the pad 56 to make substantial surface contact with the backside or underside of the receptacle 12 opposite the cavity 16.

The pad 56 has a hole 58 approximately centrally located therein. In the preferred embodiment, when the appliance 10 is brought into sealing bodily engagement with the female human form, the hollow collar 44 protrudes outwardly through the hole 58 and away from the body of the subject. As it is being used in this preferred embodiment, the appliance 10 is connected by suitable connection means 60 (such as a union) to a piece of tubing 62 having appropriate diameter and suitable resiliency. The piece of tubing 62, in turn, is connected to a fluid reservoir 64, the fluid reservoir 64 having suitable connection means 66 and clamping means 68. During the day the fluid reservoir 64 can be a leg bag, and at night can be a drainage bag. A portion of the piece of tubing 62 is normally taped to the thigh of the subject above the knee.

As the portion of the piece of tubing 62 is taped to the leg, the hollow stem 14 resists kinking at the backside or underside of the receptacle 12 opposite the cavity 16. As the hollow stem 14 is bent away from the central axis 20, first the hollow collar 44, then the hollow transitional portion 42, then lastly the hollow stem 14, deform. The relatively large thin inner diameter of the hollow collar 44 (as constrasted with that of the hollow stem 14) permits significant disposition of the drainage channel from the central axis 20, while maintaining free flow of urine out of the cavity 16. The hollow stem 14 can be bent approximately 90 degrees away from the central axis 20; and urine flowing into the cavity 16 will continue to flow out of the cavity 16 through the outlet 40 into the tubing 62.

The hole 58 in the pad 56 is slightly larger than the hollow collar 44 to allow for such bending or freedom of movement of the drainage channel or the piece of tubing 62 without kinking or binding or either.

In a preferred embodiment, manufacture of the appliance has been made using commercially available injection molding means. Normally, rubber, rubber-like or plastic urinary appliances are made by a dipping process; and it is very difficult to control wall thicknesses. In the present invention, the control of wall thicknesses of the collar, the hollow transitional portion and the hollow stem can be critically controlled by a commercially available injection molding process. In the preferred embodiment, the appliance is either made from a suitable thermoplastic rubber polymer or a medical grade elastomer (such as a liquid silicone rubber).

We claim:

1. A one-piece external female urine collection receptacle adapted to be positioned within the labia folds of the user and in contact with the vestibular tissue around the meatus defining the urethral opening, said device comprising a generally ovoid and open cup-shaped member having a cavity and a generally centrally disposed open bore opening through said member defining a vertical axis of the receptacle, the upper periphery of said member having an inner and outer adjacent generally locally outwardly protuberant exterior surfaces around the bore opening, and a substantially continuously curved ridge extending upwardly from the upper periphery of the receptacle defining the upper portions of said cavity within said receptacle, said upper periphery and ridge generally defining a generally adjacent pair of sealing surfaces, said receptacle having a substantially elliptical cross section in a plane perpendicular to the vertical axis, said sealing surfaces having a concave surface along a major axis of the elliptical cross section and a convex surface along a minor axis of the elliptical cross section said inner one of said adjacent surfaces generally disposed farther vertically relative to an outer one of said adjacent surfaces, for sealingly and continuously contacting and engaging with the labia folds and said vestibular tissue.

2. The urine collection receptacle of claim 1 including a drainage channel integral with said member at a backside thereof, extending therefrom and communicating with said bore opening; and means for preventing said drainage channel from kinking.

3. A receptacle of the type claimed in claim 2 wherein said drainage channel outlet includes a chamber, a transition portion and a hollow connecting stem all communicating with said cavity and collectively forming means for preventing kinking.

4. A receptacle of the type claimed in claim 3 wherein said chamber has a greater diameter than said transition portion which has a greater diameter than the stem.

5. A receptacle of the type claim in claim 4 wherein the wall thickness of said chamber, said transition portion and said stem are inversely proportional to their diameters, said chamber wall being thinner than said transition portion which is thinner than said stem, whereby, angular movement of said stem up to 90 degrees from its normal disposition causes a partial inversion of said chamber wall and said transition portion but retains an open bore in said stem communicating with said chamber and said cavity.

6. A urinary appliance adapted to externally sealingly engage a female human form comprising (a) a receptacle having an underside, an opening which forms a cavity, said cavity being radially oriented about a vertical central axis, said receptacle having a substantially elliptical cross section oriented in a plane perpendicular to said central axis, said receptacle having two annular sealing surfaces around the cavity, each sealing surface protruding away from said cavity said sealing surfaces having a concave surface along a major axis of the elliptical cross section and a convex surface along a minor axis of the elliptical cross section, each sealing surface having two ridges interposed between front and rear peaks, each peak being positioned proximate to a respective end of the major horizontal axis of said receptacle, the first sealing surface having a first peak to sealingly engage with the female human at a first point, said first sealing surface having a second peak adapted to sealingly engage with the female human at a second point located between the orifice of the urethra and the orifice of the vagina, said first sealing surface having a first pair of ridges, the second sealing surface being positioned substantially along the outer periphery of said first sealing surface and being blended into said first sealing surface at said first peak, said second sealing surface having a second pair of ridges generally converging at one end to form a third peak adapted to sealingly engage with the female human form at a third point located between said second point and the orifice of the vagina, said first sealing surface protruding vertically and axially farther away from said cavity than said second sealing surface said second sealing surface being horizontally offset from the first sealing surface, said first sealing surface and said second sealing surface being convexly curved and the curvature being directed outwardly and away from said cavity, said first sealing surface and said second sealing surface each having a wall sufficiently thick so that said first sealing surface and said second sealing surface each maintains its shape and does not deform when said urinary appliance is held against the female human form by pressure applied substantially along an underside of said receptacle opposite said cavity; and (b) a hollow stem being integral with said underside of said receptacle opposite said cavity, said hollow stem in fluid communication with said cavity and providing said cavity with an outlet.

7. The urinary appliance of claim 6 wherein said hollow stem is radially oriented about said central axis.

8. The urinary appliance of claim 6 or claim 7 wherein said hollow stem has a circular cross section and an inner diameter which recedes outwardly and away from said underside of said receptacle opposite said cavity.

9. The urinary appliance of claim 8 wherein said hollow stem includes a hollow transitional portion being integral therewith, said hollow transitional portion also being integral with a hollow collar, said hollow collar being integral with said underside of said receptacle opposite said cavity.

10. The urinary appliance of claim 9 wherein said hollow transitional portion and said hollow collar are each radially oriented about said central axis.

11. The urinary appliance of claim 9 or claim 10 wherein said hollow transitional portion and said hollow collar each has a circular cross section, the inner diameter of said hollow collar being greater than the inner diameter of said hollow transitional portion, said inner diameter of said hollow transitional portion being greater than said inner diameter of said hollow stem, said hollow stem having a greater wall thickness than said hollow transitional portion, said hollow transitional portion having a greater wall thickness than said hollow collar.

12. In combination with (a) a urinary appliance adapted to externally sealingly engage a female human form, said appliance having a receptacle containing a cavity, said cavity being radially oriented about a central axis; (b) an anti-kinking drainage channel being integral with a backside of said receptacle opposite said cavity and comprising a hollow stem, a hollow transitional portion integral therewith, and a hollow collar integral with said hollow transitional portion, said hollow collar also being integral with said underside of said receptacle opposite said cavity, said hollow stem communicating with said cavity and providing said cavity with an outlet, said hollow stem, said hollow transitional portion, and said hollow collar each being aligned substantially along the direction of said central axis and each having a circular cross section, the inner diameter of said hollow collar being greater than the inner diameter of said hollow transitional portion, said inner diameter of said hollow transitional portion being greater than the inner diameter of said hollow stem, said inner diameter of said hollow stem decreasing progressively receding away from said underside of said receptacle opposite said cavity, said hollow stem having a greater wall thickness than said hollow transitional portion, said hollow transitional portion having a greater wall thickness than said hollow collar; whereupon, when said hollow stem is disposed away from said central axis up to a value of about 90 degrees, said collar along with said transition portion inverts along a portion of their walls with the hollow stem opening into said collar and communication between said cavity and said outlet is maintained.

* * * * *